United States Patent
Paradis et al.

(10) Patent No.: US 12,193,970 B2
(45) Date of Patent: Jan. 14, 2025

(54) METHOD AND SYSTEM TO DETECT CHANGES IN A PATIENT'S ENDOGENOUS TEMPERATURE SET-POINT DURING EXTERNALLY INDUCED TARGETED TEMPERATURE MANAGEMENT

(71) Applicant: ZOLL Circulation, Inc., San Jose, CA (US)

(72) Inventors: Norman A. Paradis, Putney, VT (US); B. Stuart Trembly, Hanover, NH (US)

(73) Assignee: ZOLL Circulation, Inc., San Jose, CA (US)

( * ) Notice: Subject to any disclaimer, the term of this patent is extended or adjusted under 35 U.S.C. 154(b) by 0 days.

(21) Appl. No.: 18/501,595

(22) Filed: Nov. 3, 2023

(65) Prior Publication Data

US 2024/0207089 A1    Jun. 27, 2024

Related U.S. Application Data

(63) Continuation of application No. 17/219,823, filed on Mar. 31, 2021, now Pat. No. 11,844,722, which is a (Continued)

(51) Int. Cl.
*A61F 7/00* (2006.01)
*A61F 7/02* (2006.01)

(52) U.S. Cl.
CPC .... *A61F 7/0085* (2013.01); *A61F 2007/0054* (2013.01); *A61F 2007/0093* (2013.01);
(Continued)

(58) Field of Classification Search
CPC ...... A61F 2007/0054; A61F 2007/0093; A61F 2007/0094; A61F 2007/0095;
(Continued)

(56) References Cited

U.S. PATENT DOCUMENTS

| 6,413,233 | B1 * | 7/2002 | Sites | A61M 1/369 |
| | | | | 601/3 |
| 8,696,725 | B2 | 4/2014 | Kulstad et al. | |

(Continued)

FOREIGN PATENT DOCUMENTS

| JP | 2004-517661 | 6/2004 |
| WO | 2015168228 A1 | 11/2015 |

OTHER PUBLICATIONS

Akata et al., "Reliability of fingertip Skin-Surface Temperature and its Related Thermal Measures as Indices of Peripheral Perfusion in the Clinical Setting of the Operating Theatre" Anesthesia and Intensive Care, vol. 32, 2004, pp. 519-529.
(Continued)

*Primary Examiner* — Tigist S Demie
(74) *Attorney, Agent, or Firm* — ZOLL Circulation, Inc.

(57) ABSTRACT

Systems, methods and devices for utilizing heat transfer parameters or energy expenditure of devices providing controlled hypothermia, normothermia or hyperthermia to detect changes, or the absence of changes, a patient's endogenous set-point temperature; which is not available during exogenously induced targeted temperature management. A particular embodiment would allow detection of fever in patients undergoing targeted temperature managed.

18 Claims, 5 Drawing Sheets

Related U.S. Application Data continuation of application No. 16/718,428, filed on Dec. 18, 2019, now Pat. No. 11,246,747, which is a continuation of application No. 15/472,204, filed on Mar. 28, 2017, now Pat. No. 10,548,763, which is a continuation-in-part of application No. 14/642,259, filed on Mar. 9, 2015, now Pat. No. 10,568,760.

(60) Provisional application No. 62/313,928, filed on Mar. 28, 2016, provisional application No. 61/950,294, filed on Mar. 10, 2014.

(52) U.S. Cl.
CPC .............. *A61F 2007/0094* (2013.01); *A61F 2007/0095* (2013.01); *A61F 7/02* (2013.01)

(58) Field of Classification Search
CPC .... A61F 2007/126; A61F 7/0085; A61F 7/02; A61F 7/12
See application file for complete search history.

(56) References Cited

U.S. PATENT DOCUMENTS

| | | | |
|---|---|---|---|
| 2003/0078638 A1* | 4/2003 | Voorhees | A61F 7/0085 607/104 |
| 2006/0122673 A1* | 6/2006 | Callister | G05D 23/1925 607/113 |
| 2006/0190066 A1 | 8/2006 | Worthen | |
| 2007/0043409 A1 | 2/2007 | Brian et al. | |
| 2013/0030411 A1 | 1/2013 | Kreck et al. | |
| 2013/0138185 A1 | 5/2013 | Paxman et al. | |
| 2014/0213843 A1 | 7/2014 | Pilla et al. | |
| 2015/0105687 A1 | 4/2015 | Abreu | |
| 2015/0250643 A1 | 9/2015 | Paradis | |
| 2016/0331244 A1 | 11/2016 | Barton-Sweeney | |

OTHER PUBLICATIONS

Gaieski et al., "Impact of Time to Antibiotics on Survival in Patients with Severe Sepsis or Septic Shock in Whom Early Goal-Directed Therapy was Initiated in the Emergency Department", Crit. Care Med, vol. 38, No. 3, pp. 1045-1053, 2010.

Greer et al., "Impact of Fever on Outcome in Patients with Stroke and Neurologic Injury", Stroke, Oct. 27, 2008, vol. 39, pp. 3029-3035, http;//stroke_ahajournals.org/content/39/11/3029.

Holzer, "Targeted Temperature Management for Comatose Survivors of Cardiac Arrest", N. Engl. J. Med, vol. 363, No. 13, pp. 1256-1264, 2010.

International Search Report and Written Opinion dated Aug. 25, 2017 in related PCT Application US2017/024630.

Knapik et al., "Comparison of Intravascular and Conventional Hypothermia After Cardiac Arrest", Kardiologia Polska 69, pp. 1157-1164, 2011.

Mekjavic and Eiken, "Contribution of Thermal and Nonthermal Factors to the Regulation of Body Temperature in Humans", J. Appl. Physiol., 1985, vol. 100, No. 6, pp. 2065-2072, 2006.

Tanabe et al., Evaluation of Thermal Comfort Using Combined Multi-Node Thermoregulation (65MN) and Radiation Models and Computational Fluid Dynamics (CFO), Energy and Buildings 34 (2002), pp. 637-646.

Van Ooijen et al., "Cold-Induced Heat Production Preceding Shivering", British Journal of Nutrition 93, pp. 387-391, 2005.

* cited by examiner

METHOD AND SYSTEM TO DETECT CHANGES IN A PATIENT'S ENDOGENOUS TEMPERATURE SET-POINT DURING EXTERNALLY INDUCED TARGETED TEMPERATURE MANAGEMENT

RELATED APPLICATIONS

This patent application claims priority to U.S. Provisional Patent Application No. 62/313,928 entitled A Method To Detect Changes In A Patient's Endogenous Temperature Set-Point During Externally Induced Targeted Temperature Management filed Mar. 28, 2016. Additionally, this patent application is a continuation in part of copending U.S. patent application Ser. No. 14/642,259 entitled Method to Detect Changes in a Patient's Endogenous Temperature Set-Point During Externally Induced Targeted Temperature Management, filed Mar. 9, 2015, which claims priority to U.S. Provisional Patent Application No. 61/950,294 entitled Method to Detect Changes in a Patient's Endogenous Temperature Set-Point During Externally Induced Targeted Temperature Management, filed Mar. 10, 2014. The entire disclosure of each such application is expressly incorporated herein by reference.

FIELD OF THE INVENTION

The present disclosure relates generally to the fields of medicine and biomedical engineering, and more particularly, to methods, systems and apparatus which use measurements of thermal transfer or energy expenditure as a surrogate for a patient's endogenous temperature status.

BACKGROUND

Pursuant to 37 CFR 1.71(e), this patent document contains material which is subject to copyright protection and the owner of this patent document reserves all copyright rights whatsoever.

Endogenous patient set-point temperature is a function of a complex afferent system that senses environmental and endogenous needs for alterations of physiologic set-point temperature, and an efferent effector system that alters physiologic energy output through processes such as shivering and decoupling of mitochondrial respiration. (Crawshaw et al. 19-30) The organ of central importance in establishing the physiologic set-point temperature is the hypothalamus, a region of brain that interfaces between the central nervous and endocrine systems.

A patient's endogenous temperature set-point temperature is important clinically and it is one of the classic vital signs. It is generally considered the most important early indicator of infection. Early diagnosis and treatment are the most important predictors of outcome in serious infection. (Gaieski et al. 1045-53)

In intact and ill patients, the set-point temperature and the pattern with which the body responds to perturbations in temperature is complex. (Mekjavic and Eiken 2065-72) The concept of a specific universal, invariable endogenous temperature set-point is an oversimplification. Rather than a specific temperature, it is more likely that there is an interthreshold zone that the body's core temperature is maintained within. This zone is variable between individuals and has a circadian cycle within specific individuals. Hereinafter, when endogenous temperature set-point is referred to, it is understood that such reference may be to an interthreshold zone.

When the body's core temperature deviates below the interthreshold zone, a series of coordinated responses occur that include surface vasoconstriction, shivering, and metabolic thermogenesis, among others. When the body's core temperature deviates above the interthreshold zone, a series of coordinated responses occur that include surface vasodilatation and sweating, among others. Deviation from the interthreshold zone is also associated with behavioral patterns such as the seeking or avoidance of environmental heat.

In medicine, targeted temperature management, hereinafter referred to as TTM, is the artificial induction and maintenance of a specific core body temperature as a treatment for a disease or adjunct to another therapy. The temperature induced and maintained may be hypothermic, normothermic, or hyperthermic. Hypothermia is a subnormal body temperature (below approximately 37.6° C.). Normothermia is a normal body temperature (approximately 37.0°±0.4° C.). Hyperthermia or hyperpyrexia is a supranormal body temperature (above approximately 37.4° C.).

Hypothermic, normothermic and hyperthermia, TTM are becoming increasingly important in the medical management of various disease states. For instance, therapeutic hypothermia is utilized in preventing organ injury in diseases such as cardiac arrest, stroke and acute myocardial infarction. Artificial exogenously induced hypothermia is commonly used to treat coma after cardiac arrest. (Holzer 1256-64)

Hypothermia may have clinical utility in any disease state that includes ischemia-reperfusion or acute inflammation as a component of its pathophysiology. It is also utilized in the treatment of brain injury. Controlled normothermia and prevention of hyperthermia may be effective in the treatment of ischemia-reperfusion. Further, therapeutic hyperthermia may be important in improving the efficacy of drugs such as cancer chemotherapy agents and in the treatment of infection

SUMMARY

The present disclosure provides methods and systems useable to detect changes in the endogenous temperature set-point of a patient undergoing TTM, such changes in the endogenous temperature set-point being indicative of fever, effervescence, or absence of either. In certain embodiments, measurement, transformation, and/or presentation of the energy or thermal requirements needed to maintain the patient at a specific target temperature are provided. Alternatively, in some embodiments, a algorithmic combination of the thermal input or output, temperature of the cooling/heating transfer subsystem, along with environment temperature, and patient specifics, may be utilized.

In accordance with certain aspects, there are provided methods and systems for controlling a patient's body temperature and determining any change in the patient's endogenous set point temperature. A system according to such aspects may comprise a heat exchange device which exchanges heat with the subject's body and control apparatus for controlling the heat exchange device to maintain the patient's body temperature at a predetermined target temperature or within a predetermined target temperature range in combination with one or more sensors and apparatus for determining changes in the amount of energy required to maintain the patient's body temperature at the predetermined target temperature or within the predetermined target temperature range, such changes being indications of changes in the patient's endogenous set point temperature.

The body heat exchange device may any type of body heat exchange device, including but not limited to body surface heat exchange systems (e.g., blankets, pads, garments, etc.) or endovascular heat exchange devices (e.g., heat exchange catheter systems). [0004] Examples of body surface heat exchange systems include the STx Surface Pad System (ZOLL Circulation, Inc., San Jose, California), the ARCTIC SUN 5000 Temperature Management System (Bard Medical Division, Covington, Georgia), the Criticool System (MTRE Advanced Technologies, Ltd., Feasterville-Trevose, Pennsylvania) and the BAIR HUGGER, BAIR PAWS and POLAR AIR Systems (3M, St. Paul, Minnesota). Examples of commercialized endovascular heat exchange systems include the Thermogard XP Temperature Management System (ZOLL Circulation, Inc., San Jose, California) and InnerCool RTx Endovascular Temperature Modulation System (ZOLL Circulation, Inc., San Jose, California).

Further, detected changes in the patient's endogenous set point temperature may be used as a basis for diagnosing a change in the patient's febrile status. Potential changes in the patient's "febrile status" include a) onset of a fever in a previously non-febrile patient, b) cessation of a fever in a previously febrile patient, c) an increase in the severity fever in a previously febrile patient and/or d) a decrease in the severity of fever in a previously febrile patient. In certain embodiments, systems may include processors programmed to analyze the sensed changes in the patient's set point temperature, correlate those changes to changes in the patient's febrile status and optionally issue an indication, alarm or other notification of change in the patient's febrile status. Still further aspects and details of the present invention will be understood upon reading of the detailed description and examples set forth herebelow.

BRIEF DESCRIPTION OF THE DRAWINGS

The following figure is included in this patent application and referenced in the following Detailed Description and Examples. This figure is intended only to illustrate certain aspects or embodiments of the invention and does not limit the invention in any way.

DETAILED DESCRIPTION

Figure 1:
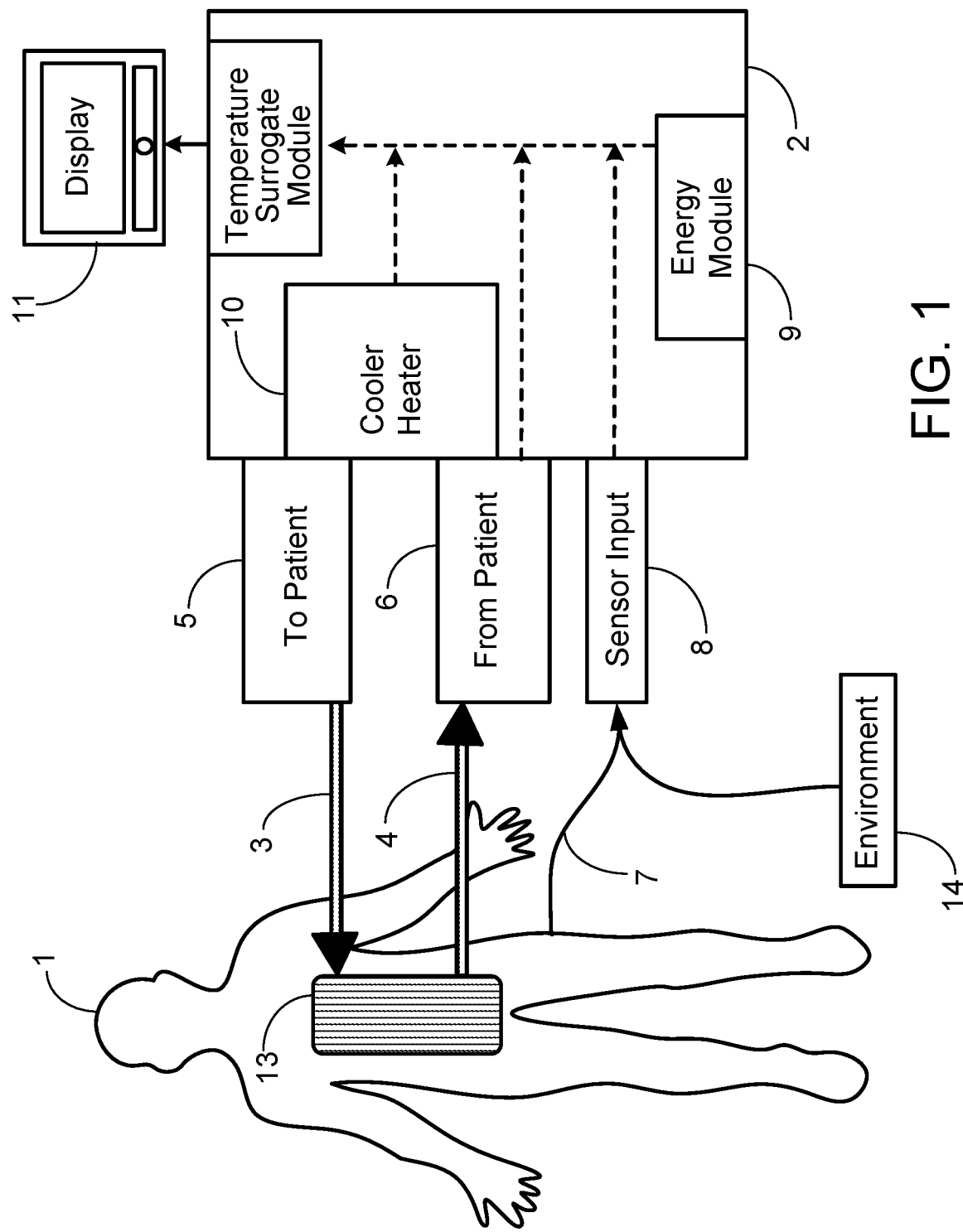
FIG. 1 is a diagrammatic representation of one embodiment of a method of the present invention.

The following detailed description and the accompanying drawings to which it refers are intended to describe some, but not necessarily all, examples or embodiments of the invention. The described embodiments are to be considered in all respects only as illustrative and not restrictive. The contents of this detailed description and the accompanying drawings do not limit the scope of the invention in any way.

There are a number of methods for inducing and maintaining hypothermic, normothermic, or hyperthermic TTM. A typical TTM device is comprised of a subsystem to affect heat transfer between the TTM device and a patient, sensing and control mechanisms for managing the heat transfer, and a heating-cooling unit.

The subsystem to affect heat transfer may include one or more components, such as a catheter, a blanket or adhesive pads, and a heat-transfer fluid. The components of this subsystem are generally designed to optimize the efficiency of heat transfer, and may utilize a temperature-controlled fluid, such as water or saline, supplied to one or more components, such as a catheter, a blanket or an adhesive pad.

The control subsystems generally utilize negative feedback mechanisms. When an event occurs wherein the patient's temperature deviates from the intended target temperature, the event is detected by the sensing subsystem. The heating-cooling and heat transfer subsystems are then adjusted so as to return the patient's temperature to the target temperature. To avoid oscillation, the control system may include feed-forward and dampening algorithms.

The control system is generally computer based, and may be comprised of a sensing subsystem, feedback control and dampening mechanisms, and interfaces with the heat-transfer and heating-cooling subsystems. Standard electrical devices, generally incorporating circuit boards, semiconductor chips and transistors, are available to perform these functions.

The sensing subsystem will generally incorporate a thermometer or thermistor within or upon the patient and a electrical connection to the control subsystem.

The heating-cooling unit of a typical TTM device is generally a variation on widely available heating and refrigeration devices.

Hypothermia may have clinical utility in any disease state that includes ischemia-reperfusion or acute inflammation as a component of its pathophysiology. It is also utilized in the treatment of brain injury. Controlled normothermia and prevention of hyperthermia are also potentially effective in the treatment of ischemia-reperfusion. Further, therapeutic hyperthermia may be important in improving the efficacy of drugs While TTM may improve the outcome of patient suffering from various disease states, it makes the patient's endogenous set-point temperature—an important clinical vital sign—unavailable to the clinicians caring for the patient. Depending on the responsiveness, power and sophistication of the device providing TTM, the patient's measurable temperature may deviate from the target temperature by an amount that is not detectable by clinicians.

Inability to detect changes in a patient's endogenous set-point temperature can have negative effects on the clinical outcome of patients. The inflammation that heralds the onset of an infection is normally detected by the onset of fever. The inability to detect changes in the patient's endogenous temperature set-point may delay the detection of a fever and subsequent diagnosis and treatment of an infection. It is currently believed that the single most important determinant of outcome in life threatening infection is the time from onset of infection to initiation of therapy with appropriate antibiotics.

In general, TTM will mask, or make more difficult to detect, endogenous temperature changes when patients suffer infection or other disease states that are associated with an alteration in the endogenous temperature set-point. Sepsis, for instance, is often associated with endogenous hypothermia. Failure to detect the endogenous hypothermia may delay the diagnosis of sepsis leading to a worse outcome.

It is common during TTM to administer drugs that induce neuromuscular blockade along with appropriate sedation.

These medications will assist in temperature control but will also act to mask or completely ablate shivering. This renders the detection of fever onset more difficult.

The relationship between a patient's ESPT (interthreshold zone), actual body temperature and the device providing TTM are is complex and includes the following parameters to greater or lesser degree:
1. ESPT or interthreshold zone
2. Circadian rhythm for temperature
3. Specific illness or injury
4. The extent of neuroinjury
5. The degree of sedation
6. The degree of neuromuscular blockade
7. Ambient room temperature
8. Local convection and or radiation heating or cooling
9. Presence and degree of ventilator heating
10. The degree of evaporative cooling from the skin or respiratory tract
11. Presence of blankets, clothing or other covering
12. Patient weight or body habitus
13. Patient capacity to shiver
14. Cooling or heating via administered intravenous fluids above or below body temperature.
15. Pharmacotherapy with drugs that affect ESPT such as aspirin or acetaminophen among others.

There have been significant advances in the development of medical diagnostics. Of particular relevance, machine learning derived multivariable algorithms constructed from the measurement of multiple individual parameters have been widely applied. (Kato 248-51) Useful mathematical diagnostic algorithms may be developed using the in silico techniques variously called machine learning, data mining, and big data, among other terms.

The phenomena that the performance of machine learning derived algorithms is principally dependent on the input measurements and independent of the specific in silico software routine used for its derivation. If the same training data set is used, techniques as different as supervised learning, unsupervised learning, association rule learning, hierarchical clustering, multiple linear and logistic regressions are likely to produce algorithms whose clinical performance is indistinguishable.

Because TTM effectively takes control of a patient's body temperature, a patient may suffer from a fever without such fever being manifest by a measureable rise in patient's body temperature. Consequently, in patients undergoing TTM, typical body temperature measurements may not be relied upon as indicators of the patient's endogenous set-point temperature vital sign and, as a result, detection and diagnosis of the onset or worsening of a fever-inducing condition, such as an infection, may be delayed.

The embodiments disclosed herein restore the ability of clinicians to detect, diagnose, and treat diseases associated with changes in endogenous set-point temperature. In particular, it will be useful in the diagnosis of fever and infection in patients undergoing external cooling. This would allow earlier administration of antibiotics, which would be associated with improved patient outcomes.

In certain embodiments, the use of the energy or heat transfer parameters of a TTM device as a surrogate for changes in endogenous temperature set-point, or their use in early diagnosis of fever and infection are described herein.

With reference to FIG. 1, during TTM, measurement of the body temperature vital sign may not be relied upon as an indicator of a patient's endogenous set-point temperature. However, a change in the patient's endogenous temperature set-point may be detected as a change in: 1) the energy of warming or cooling 10 required to maintain the therapeutically targeted temperature, 2) the volume and/or temperature of the heat-transfer fluid 3, 3) the energy expenditure of the heat-cooling subsystem 9 and 10, or a combination of these.

A change in the patient's endogenous temperature regulation and set-point, might also first be detected by a change in the temperature of fluid 4 being returned to the TTM device 2.

As an example of the clinical application—when the TTM device is being utilized for maintenance of controlled hypothermia or normothermia, the onset of fever in a patient will be detectable as a need to provide additional cold, or colder, fluid, to the heat-exchange subsystem 13 and an associated increase in the energy requirement 9 of the TTM's 2 refrigeration module 10. The abatement of fever, defervescence, would be detected by the opposite of these events.

Similarly, when the TTM device is being utilized for maintenance of controlled hyperthermia, the onset of fever in a patient will be detectable as a need to provide less warm fluid 3 to the heat-exchange subsystem 13 and an associated decrease in the energy expenditure of the TTM device. Again, the abatement of fever would be detected by the opposite of these events.

The changing requirements for cooler or warmer heat transfer fluid at the onset of infection and fever, and the associated difference in the energy requirement of the TTM device 2, may be presented as data to assist clinicians. Further, the different requirements to provide cold or warm fluid or the difference in the energy required by the TTM device could be plotted against time, or change from baseline, and displayed graphically 11.

The different requirements to provide cooler or warmer fluid or the difference in the energy required by the TTM device may be combined with other data, for e.g. measurements of metabolism or physiology, to derive an earlier or more accurate assessment of a patient's endogenous temperature regulation.

The different requirements to provide cooler or warmer fluid 3 or the difference in the energy required by the TTM 2 device may, with or without combination with other data, be utilized in an algorithm 11 to predict impending shivering and deploying counter-shivering therapies. These therapies may include control of the TTM device itself to alter the speed with which alteration in TTM are effected.

The different requirements to provide cooler or warmer fluid, or the difference in the energy required by the TTM device to maintain the therapeutic target temperature may, with or without combination with other data, be presented visually to assist clinicians 11. Particular embodiments of this visual presentation may include, but are not limited to, the variables as a function of time, or change from baseline.

To improve the accuracy of the system in detecting changes in patient endogenous set-point temperature, the environment temperature 14, or changes in the environment temperature 14, may be incorporated into the algorithm utilized.

The conversion of measured energy expenditure or transfer fluid temperature to an artificial surrogate for changes in patient temperature is a variant of classic heat transfer:

$$Q = mc\Delta T$$
Heat transfer = (mass)(specific heat)(temperature change)

Q = heat content in Joules
m = mass
c = specific heat
T = temperature
ΔT = change in temperature Inclusion of a general purpose computer within the system would allow solution of this problem. Utilization of more advanced nonlinear and multivariable models would likely be associated with improved performance in the algorithms utilized.

By way of example, but not limitation, a mode may include:

1. A component that measures the temperatures and volumes of the fluid utilized by the heat transfer subsystem of the device providing TTM. Techniques for measurement of temperature are well know and include thermometers, thermistors, and infrared detectors, among others. Techniques for measurement of fluid flow are also well know and include flow meters of various design. Standard electrical devices, generally incorporating circuit boards, semiconductor chips and transistors, are available to perform these functions.
2. A component that measures the energy utilized by the cooling or warming subsystem of the device providing TTM. Standard electrical devices, generally incorporating circuit boards, semiconductor chips and transistors, along with thermistors, are available to perform the necessary functions.
3. A component that transforms said measurements into a clinically useful surrogate representative of the patient's endogenous set-point temperature and changes in this parameter over time. The latter would function as a surrogate diagnostic of fever. These results may be presented graphically. Standard electrical devices, generally incorporating circuit boards, semiconductor chips and transistors, along with a general purpose computer and video presentation technology, are available to perform these functions.

Methods for the derivation of a multivariable algorithm for detection of changes in endogenous set-point temperature based on measurements of fluid transfer temperatures, fluid transfer volumes, heating or cooling energy requirements, or a combination of these parameters, would be devisable by skilled practitioner in the art of heat transfer and mathematical modeling. By way of example, but not limitation, additional refinements that could be constructed include:

1) A diagnostic biomarker of neuroinjury or a prognostic biomarker predictive of neurologic outcome based on the energy or heat transfer parameters or patterns of the TTM device. Additionally, these measurements may be combined with others in a multivariable algorithm.
2) A diagnostic biomarker of neuroinjury or a prognostic biomarker predictive of neurologic outcome based on the energy or heat transfer parameters or patterns of the TTM device after the device has attempted to perturb the patients ESPT with a known thermal load. Again, these measurements may be combined with others in a multivariable algorithm.
3) A multivariable algorithm that detects changes in the patient's ESPT more accurately than the energy or heat transfer parameters alone. Among the other parameters that might be used in such an algorithm might be:

Indicators of the degree of neuroinjury measured by alternative means such as the electroencephalogram or evoked potentials among others.

Indicators of the degree of sedation measured by alternative means such as Bispectral index, skin conductance, surface electromyogram, evoked potentials, among others.

Indicators of the degree of neuromuscular blockade such as train-of-four stimulations or other similar techniques.

Measurements of cutaneous vasoconstriction or vasodilatation

Measurements of sweating

Indicators of the degree of shivering, such as electromyography or other similar techniques.

Indicators of ambient room temperature.

Indicators of ventilator heating

Indicators of the degree of evaporative cooling from the skin or respiratory tract Patient weight or body habitus Measurements of cooling or heating via administered intravenous fluids above or below body temperature Pharmacotherapy with drugs that affect ESPT such as aspirin or acetaminophen among others The degree of evaporative cooling from the skin or respiratory tract The presence of blankets, clothing or other covering The patient's weight or body habitus Cooling or heating via administered intravenous fluids above or below body temperature.

Modifiers specific to the actual disease state

Figure 2:
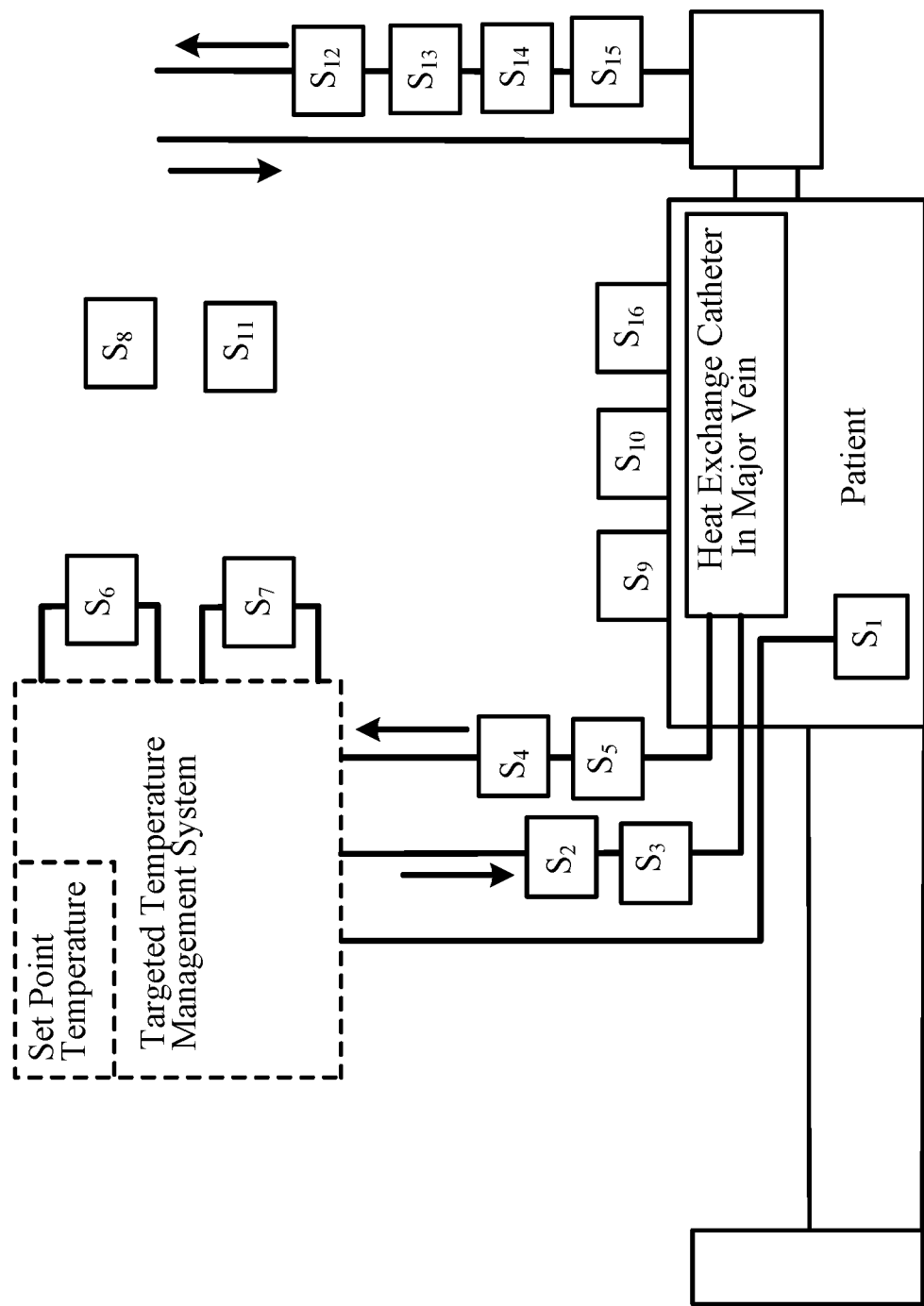
FIG. 2 is a diagrammatic representation of one embodiment of a system of the present invention.

FIG. 2 shows a patient being treated by a Targeted Temperature Management (TTM) system. As is customary with such systems, sensor $S_1$ measures the core temperature of the patient from its position, for example, within the patient's body, within the bladder of the patient, within the esophagus, or rectally. In other embodiments, sensor $S_1$ may be positioned within a blood vessel of the patient, e.g., at or near the distal tip of a heat exchange catheter placed within a blood vessel of the patient. The TTM system compares the value of patient core temperature to the value of the TTM Set Point Temperature specified by the physician treating the patient, then adjusts the temperature of the coolant flowing through heat exchange catheter placed within a major vein of the patient so as to reduce the difference between the patient core temperature and the Set Point Temperature.

For example, the physician would choose a Set Point Temperature below body temperature in order to deliver hypothermia therapy to a patient, as disclosed herein. At the beginning of such therapy, the patient's core temperature would be far above the Set Point Temperature, and the TTM system would apply significant power to the chiller system within it, so as to reduce significantly the temperature of the coolant flowing through the heat exchange catheter within the patient. The degree of reduction of the coolant temperature is accomplished according to algorithms known in control theory, such as Proportional Control, Proportional-Integral Control, and Proportional-Integral-Derivative Control (Bishop, 2011). A self-correcting system such as this is known as a control loop or, synonymously, a feedback loop.

The subsequent heat exchange process and control process reduces the core temperature of the patient until such time that the core temperature substantially equals the Set Point Temperature. This hypothermic core temperature then is maintained for as long as the physician determines; this occurs in spite of perturbing influences, such as changes in the room temperature, the covering and uncoverings of the patient, the possibly changing neurological condition of the patient, and the onset of a fever in the patient.

In one embodiment, sensor $S_2$ (FIG. 2) measures the temperature of the TTM system coolant flowing into the patient and sensor $S_4$ measures the temperature of the TTM system coolant flowing out of the patient. Sensors $S_3$ and $S_5$ measure the volume flow rate of the TTM coolant flowing into and out of the patient, respectively; alternatively, one of these sensors may be eliminated from the system, under the assumption that no leaks are present in the coolant flow path. These sensors, by their nature, may produce a continuous, analog voltage, in which case the processor will contain an Analog-to-Digital Converter (ADC), a known electronic sub-system. The ADC produces digital data at fixed time intervals that encodes the analog signals from the sensors. The steady flow of digital data can be manipulated by a Central Processing Unit (CPU), or an equivalent electronic sub-system, so as to perform calculations with the digital data. In this way, the Processor scheme diagramed in FIG. 3 periodically will compute the cooling power, $P_{cool}$ delivered to the patient, according to the known expression (Mills, 1999).

$$P_{cool} = c_p \rho w (T_{outflow} - T_{inflow})$$

wherein $c_p$ is the specific heat of the coolant at constant pressure (in joules/(kg °C.)), $\rho$ is the coolant density (in kg/m$^3$), w is coolant flow rate (in m$^3$/sec), $T_{inflow}$ is the coolant inflow temperature (in °C.) measured by sensor $S_2$, and $T_{outflow}$ is the coolant outflow temperature (in °C.) measured by sensor $S_4$.

In an alternative embodiment, the signals from the sensors remain in analog form, then are manipulated in the Processor by known analog electronic devices, such as operational amplifiers, so as to perform the calculation defined above.

Figure 3:
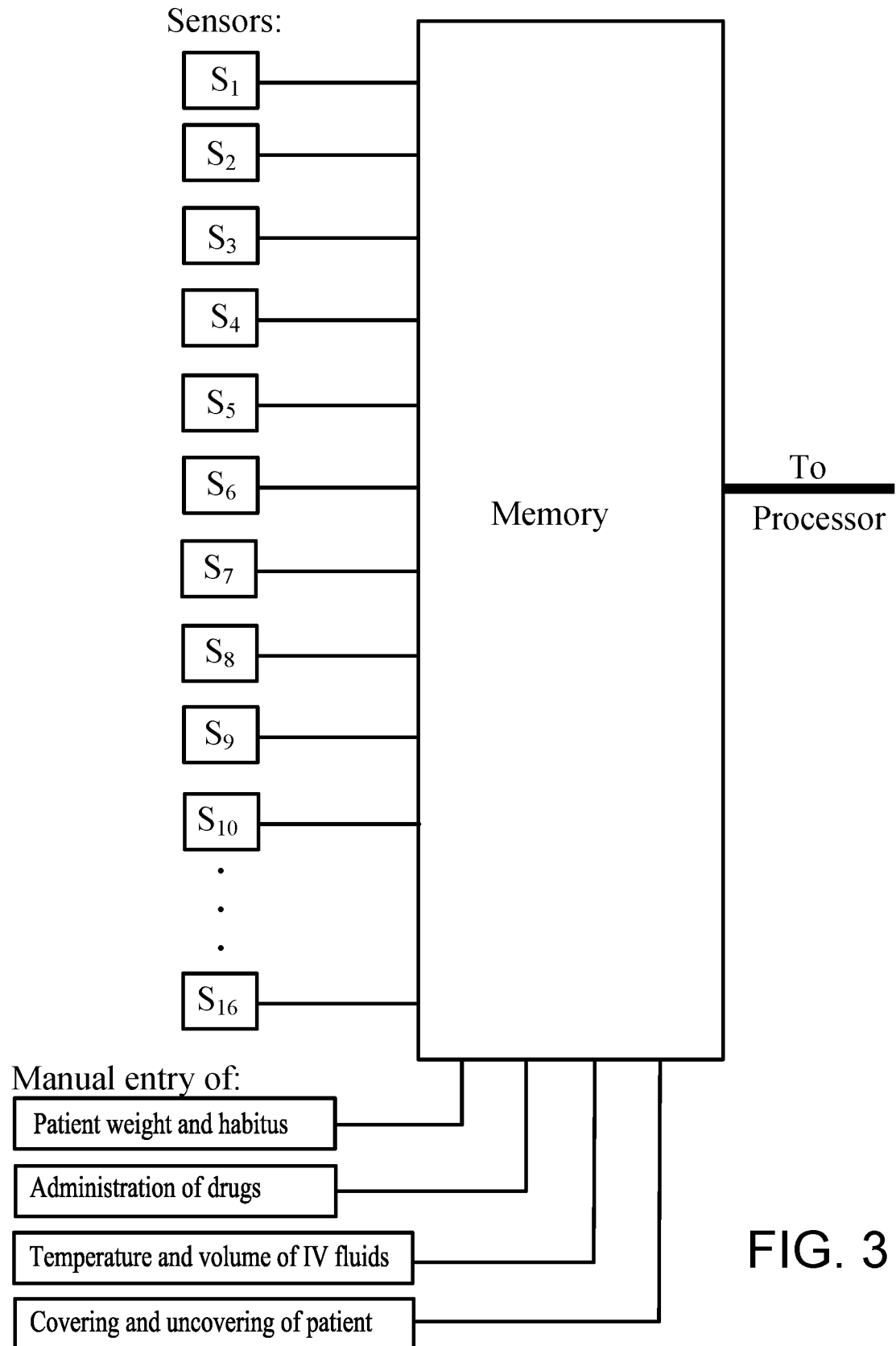
FIG. 3 shows an example of a processor scheme useable in systems of the present invention.

The parameters $c_p$ and $\rho$ may be treated as known constants, with values stored in the system Memory (FIG. 3). Alternatively, these quantities $c_p$ and $\rho$ may be treated as slowly-varying functions of temperature, as is the case in reality (Mills, 1999) in order to make a slightly more accurate calculation. Then, for each calculation of $P_{cool}$, a look-up table stored in the system Memory will be consulted to associate a value of $c_p$ and $\rho$ with the current average temperature of the coolant, equal to $T_{average}=(T_{inflow}+T_{outflow})/2$; alternatively, empirical formulas may be used to compute values of $c_p$ and $\rho$ from the current value of $T_{average}$.

The current value of $P_{cool}$ is stored in system Memory and may be displayed in numerical form on a meter on a panel visible to the physician; in one embodiment the meter is digital, in another, the meter is analog. To provide greater context to the physician, the current and past values of $P_{cool}$ may be displayed graphically on a system display, a computer screen and/or on a remote receiver device such as a remotely located computer, tablet or smartphone device; and the past values may extend back in time for several hours or several days, at the option of the physician. In one embodiment, a separate line displayed upon the graph of values of $P_{cool}$ may be positioned at a constant value known to be associated with a typical fever. This value would equal a value some known number of watts above the baseline value of $P_{cool}$ for the patient, where the baseline value can be defined as that present for the most recent several hours, such as four hours, provided that was constant to within a specified maximum deviation, such as ±10%.

As disclosed herein, a TTM system may prevent any measureable rise in the core temperature of a patient with a fever. However, it cannot do so with out removing the significant, incremental heat produced by the newly-febrile patient. In this way, the graphical display of values of $P_{cool}$ may clearly signal the onset of a fever in the patient, particularly when the value of $P_{cool}$ has suddenly increased by an amount exceeding a value known to be associated with a fever. The heating power associated with a fever may be calculated from a known expression of the conservation of energy, namely $P_{fever}=Mc_p \, dT_{core}/dt$ (Mills, 1999), where M is the mass of the patient, $c_p$ is the effective specific heat of all body tissues, and $dT_{core}/dt$ is the rate of increase of the core temperature of the patient at the onset of fever. A typical value of $dT_{core}/dt$ is given by, (Hall, 1996, see FIG. 73-11), as approximately 1.5° C./hour, a typical patient mass is 70 kg, and body tissues approximately have the specific heat of water, the exact value being somewhat less. Then the power associated with a fever equals approximately 122 watts, with the understanding that normal biological variation will produce a range of values of fever power in the clinic.

In one embodiment, an alarm or alert indicator visible, audible or otherwise perceivable within the patient's room will be triggered when such an event, such as a change in the patient's endogenous temperature set-point and/or febrile status, occurs. Alternatively or additionally, such alarm or alert may be transmitted by wired or wireless connection to, and emitted by, one or more alarm emitting devices perceivable within the patient's room and/or at remote locations. Nonlimiting examples of the types of alarm or alert emitting devices may include but are not limited to one or more of:
a display or emitter that is included in the TTM system;
a portable alarm module that is a component of the TTM system;
a separate electronic monitor;
a patient bedside monitor;
a monitor located remotely from the patient's bedside.
a central unit monitoring station; and
a remotely located computer, tablet computing device, pager, or smartphone.

In another embodiment, an electrical alarm signal will be sent to an electronic communication system when such an event occurs. In certain embodiments, an alarm or alert may be a, e.g., visual, auditory, or electrical signal sent to a machine or device, e.g., a phone, smartphone, watch or other computer that is local or remote relative to the patient. The alarm or alert signal may be received in the patient's room, or in some other location in a hospital or in a remote location outside of the hospital, by a physician, nurse or other caregiver.

In one embodiment, the one or more of sensors $S_2$, $S_3$, $S_4$, and $S_5$ are installed in the flow path of the TTM coolant using quick-disconnect connectors, for example, the commercial brand of Luer Lock connectors. Such quick-disconnect connectors are used in commercial TTM systems, because a new heat transfer catheter must be connected to the TTM system itself when each patient is treated. Specifically, the connection between the sensors and the TTM system itself is made with quick-disconnect connectors, and the connection between the sensors and the heat transfer catheter is made with quick-disconnect connectors. Each such connector is chosen to be compatible with the specific type used in commercial TTM systems. In this way, the sensors $S_2$, $S_3$, $S_4$, and $S_5$ may be installed in line with the existing elements of a commercial TTM system without disrupting its operation and without mechanical modification of it. For example, sensors $S_2$, $S_3$, $S_4$, and $S_5$ and the other system elements taught in this disclosure could form a free-standing system that could be sold separately from the TTM system.

In one embodiment, Sensor $S_2$ is installed within the heat transfer catheter at a location proximate to the upstream margin of the portion of the catheter through which heat transfer from venous blood is intended to take place; one example of proximate is a separation of 1 mm, and another example of proximate is 10 mm. Similarly, the Sensor $S_4$ is installed within the heat transfer catheter at a location proximate to the downstream margin of the portion of the catheter through which heat transfer from venous blood is intended to take place; one example of proximate is a separation of 1 mm, and another example of proximate is 10 mm. In this embodiment, the temperature difference measured by Sensors $S_2$ and $S_4$ is substantially equal to the true value, in that the known phenomenon of counter-current heat exchange has not reduced the measured temperature difference to a smaller value than the true value (Mills, 1999).

In one embodiment, an experimental study of counter-current heat exchange in each particular model in the heat exchange catheter is made, so as to relate two temperature differences: (a) that measured by Sensors $S_2$ and $S_4$ when located proximate to the portion of the catheter where heat exchange from venous blood is intended to take place, and (b) that measured by Sensors $S_2$ and $S_4$ when not located proximate to the portion of the catheter where heat exchange from venous blood is intended to take place. An example of the later locations for Sensors $S_2$ and $S_4$ is at the proximal end of the heat exchange catheter, where the catheter connects to the TTM system. It is advantageous to locate $S_2$ and $S_4$ in this proximal location, because the electrical leads of the sensors need not run along most of the length of the catheter.

Another advantage is that all or many existing commercial heat exchange catheters do not have any thermometry sensors installed within them. In order to use these same catheters in conjunction with the system disclosed herein, it is desirable to know how the temperature differences defined above are related. For a defined geometry of the heat exchange catheter, a defined coolant flow rate within the heat exchange catheter, and a fixed temperature of still ambient air, the relationship between the two temperatures defined above is a monotonic relationship that can be determined by experiments (Mills, 1999).

In an alternative embodiment, the heat exchange catheter incorporates a thermally insulating layer between the inflow path of coolant and the outflow path of coolant. This layer will reduce the counter-current heat transfer between the adjacent flow paths, thus making a measurement of the temperature difference by Sensors $S_2$ and $S_4$ located near the point of connection of the heat exchange catheter and the TTM system more accurate than otherwise.

In an alternative embodiment, the portion of the heat exchange catheter that is exterior to the patient is covered with an insulating material, so as to reduce heat transfer from ambient air. This is advantageous, because this will reduce the spurious effect of varying temperature of ambient air on the measurement of the temperature difference by Sensors $S_2$ and $S_4$ located near the point of connection of the heat exchange catheter and the TTM system.

It is known that $P_{cool} = c_p\, \rho\, w\, (T_{outflow} - T_{inflow})$, as defined above. For a given value of $P_{cool}$, it follows that a smaller value of coolant flow rate w will be associated with a larger value of the temperature difference $(T_{outflow} - T_{inflow})$, all else being equal; the converse also is true. In one embodiment, the value of w in the TTM system will be set equal to or, for example, within 20% of the lowest practical value, so as to increase the temperature difference $(T_{outflow} - T_{inflow})$, with the intent of detecting the onset of a fever with greater certainty. The lowest practical value of w is defined in the following paragraph. Given that each of the measured values of $T_{outflow}$ and $T_{inflow}$ must contain a random component due to noise, it is true that their difference must also have a random component. By making the difference $(T_{outflow} - T_{inflow})$ larger, the random contribution of noise therein is reduced proportionally, thus making greater the chance of a correct diagnosis of the onset of a fever. This follows from the known advantage of a large Signal-To-Noise Ratio (SNR) (Schafer, 1989).

For a full appreciation of the role of coolant flow rate w in increasing the value of SNR, it must be understood that the value of w must not be so small that the value of $T_{inflow}$ drops to a value near the freezing point of the coolant. Cessation of patient cooling would follow, if the coolant flow path were blocked internally by frozen coolant; alternatively, a separate flow path within the chiller system of the TTM system could become blocked, with the same effect. Generally, the value of $T_{inlet}$ must decrease in order to increase the value of $P_{cool}$, especially if the value of $T_{outlet}$ is understood to equal approximately the core temperature of the patient; this would be true if the coolant substantially attained thermal equilibrium during its passage through the heat transfer catheter. It follows that the control algorithm of the TTM system will require a sudden decrease in the TTM coolant temperature (defined as $T_{inlet}$ in reference to the patient) upon the onset of a fever, in order to cancel the heat associated with the fever. The decrease in $T_{inlet}$ will be larger, the smaller the value of w, and this fact is advantageous for detection of the fever, as described above. However, the value of w must not be set lower than a minimum practical value, this being the value that would cause $T_{inlet}$ to fall near the freezing point of the coolant.

In an alternative embodiment valued for its simplicity, Sensor $S_2$ measures the temperature of the TTM coolant flowing from the TTM system toward the heat exchange catheter in the patient; no calculation of cooling power, $P_{cool}$, is made by the Processor. The values of TTM coolant temperature are stored in Memory, and the current and recent values of TTM coolant temperature are displayed, as described above. Optionally, the processor filters the values of TTM coolant temperature with a suitable low-pass filter, so as to produce values characteristic of the most recent several minutes, as opposed to rapidly-varying instantaneous values. The physician interprets this display with the understanding that a sudden decrease in the coolant temperature, $T_{inlet}$, may signal the onset of a fever in the patient. The Processor will display a value of coolant temperature known from theoretical calculations and clinical observations to be a value associated with the onset of fever within a patient. The alarm functions described above will become active when the TTM coolant temperature falls below the value known generally to be associated with the onset of a fever. In this embodiment, the coolant temperature, $T_{inlet}$, is measured by a thermometry sensor connected between the TTM system and the heat exchange catheter with quick-disconnect connectors that are chosen to be compatible with the connectors of the TTM system and the heat exchange catheter.

It will be appreciated that fundamental physical considerations imply that values of $P_{cool}$ will be greater during times of cool-down in the patient. This follows from a statement of energy conservation for the patient, M $c_p$ $dT_{core}/dt = -P_{cool} + P_{metabolic} - (T_{core} - T_{ambient})/R$, where M is the mass of the patient, $c_p$ is the specific heat at constant pressure of all body tissue of the patient, $dT_{core}/dt$ is the time rate of change of temperature of the patient, $P_{cool}$ is the cooling power delivered to the patient by the TTM system, $P_{metabolic}$ is the metabolic heating within the patient, $T_{ambient}$ is the air temperature around the patient, and R is the total thermal resistance between the core of the patient and the ambient air, as determined by conductive and convective heat transfer processes at and near the surface of the patient and the coverings of the patient. In a state of equilibrium before TTM begins, $dT_{core}/dt=0$ and $P_{cool}=0$, from which it follows that $P_{metabolic}=(T_{core}-T_{ambient})/R$, with $T_{core}=37°$ C., normal body temperature. This equation simply defines the value of $P_{metabolic}$ that will maintain normal body temperature in the absence of sweating, shivering, or heating due to exercise.

In the instant following application of TTM for hypothermia, $P_{cool}$ must equal a value determined by the quantity $M\ c_p\ dT_{core}/dt$, because the equation $P_{metabolic}=(T_{core}-T_{ambient})/R$ still applies before $T_{core}$ attains lower values than normal body temperature. This initial value of $P_{cool}$ can be computed from $M\ c_p\ dT_{core}/dt$, using a value of $dT_{core}/dt=0.4°$ C./hour, as reported in a clinical study (Knapik et al., 2011). With approximate values of M=70 kg and $c_p$=4180 joule/(kg ° C.) for water, we have PC, =32 watts, approximately. With another protocol that uses a higher rate of cool-down, the associated value of $P_{cool}$ would be proportionally greater.

As discussed above, the display of an increased value of $P_eOd$ in general can signal the onset of a fever. In one embodiment, we make the diagnosis of a nonexistent fever less likely by displaying the value of $M\ c_p\ dT_{core}/dt$ at all instants of time, optionally filtered by a suitable low-pass filter, as described above. If $P_{cool}$ were at some moment to increase by an amount equal to the separately-displayed value of $M\ c_p\ dT_{core}/dt$, then the increase of $P_{cool}$ could be attributed correctly as the cause of steady cooling-down of the patient and thus would not be associated with a nonexistent fever.

In one embodiment, the coolant flow rate will be increased to a value substantially larger than the minimum practical value discussed above at those times when the patient is to be cooled to some lower temperature, as part of therapy. As discussed above, greater cooling power is associated with a non-zero and negative value of $M\ c_p\ dT_{core}/dt$, and furthermore the value of cooling power is given by $P_{cool}=c_p\ p\ w\ (T_{outflow}-T_{inflow})$, as defined above. To produce sufficient cooling power for steady lowering of the patient's core temperature without causing $T_{inflow}$ to approach the freezing point of the coolant, the value of coolant flow rate, w, may be increased advantageously. When the patient has attained the desired hypothermic temperature, the value of coolant flow rate, w, can be reduced so as to increases the likelihood of detecting a fever, as discussed above.

In one embodiment, an estimate of the quantity $P_{ccol}$ will be computed from measurements made by sensors $S_6$ and $S_7$ (FIG. 2), which measure, respectively, the voltage across and the current through the chiller system present within the TTM system. The power consumed by the chiller system equals the known formula, $P_{chiller}=V_{DCchiller}\ I_{DCchiller}$, where $V_{DCchiller}$ is the DC voltage across the chiller, $I_{DCchiller}$ is the DC current through the chiller, and DC refers to a signal of one polarity (direct current). For the case of sinusoidal signals applied to the chiller system (AC signals, alternating current), the known formula is $P_{chiller}=(½) V_{ACchiller}\ I_{ACchiller}$, where $V_{ACchiller}$ is the zero-to-peak amplitude of the sinusoidal voltage across the chiller, and $I_{ACchiller}$ is the zero-to-peak amplitude of the sinusoidal current through the chiller. A chiller system may not be perfectly efficient, in that the thermal cooling power delivered to the patient is given by $P_{cool}=\varepsilon\ P_{chiller}$, where $\varepsilon$ is commonly called the efficiency factor and equals a number less than one. To account for imperfect efficiency, the Processor will compute an estimate of $P_{cool}$ from $P_{chiller}$, using the formulas immediately preceding and the known value of E, provided, for example, by the manufacturer of the chiller system. These estimated values of $P_{cool}$ can be stored in Memory (FIG. 4) and displayed as described in the paragraphs immediately above.

In one embodiment, Sensor $S_6$ (FIG. 2) measures the temperature of the ambient air at a representative location in the vicinity of the patient. These values of air temperature require no processing and are stored in the Memory, then displayed as described above for display of the current and past values of cooling power, $P_{cool}$. A physician will find the display of current and past air temperature values useful, because, for example, a sudden increase in ambient air temperature must cause the TTM system to increase its cooling power, in response to necessarily greater heat transfer into the patient from the warmer room air. With the simultaneous display of past and present values of cooling power and ambient air temperature, the physician can associate cause and effect and thus not erroneously associate the increase of cooling power, $P_{cool}$, with a nonexistent fever.

In one embodiment, Sensor $S_9$ (FIG. 2) is an electromyography sensor secured on the skin over a muscle of the patient, for example, the pectoralis muscle, which is easily accessible in the supine patient and is known to be involved in shivering (van Ooijen et al., 2005). In some embodiments, the electrical signal from this sensor may be filtered by a suitable low-pass filter in the Processor, so as to emphasize the presence of shivering from minute to minute, as opposed to the instantaneous magnitude of each muscle contraction. The past and current signals originating from Sensor $S_9$ are stored in Memory (FIG. 4), then are displayed as described above for the TTM cooling power signal, $P_{cool}$. The display of values of the signal from Sensor $S_9$ is valuable to the physician, because shivering adds thermal energy to the patient, which will stimulate a compensating increase in the value of the cooling power, $P_{cool}$, generated by the TTM system. If shivering occurred at a past time, when no direct clinical observation of shivering was possible, then the display of past values produced by sensor $S_9$ may permit the physician to associate cause and effect and thus not associate a past increase in $P_{cool}$ erroneously with a nonexistent fever. In an alternative embodiment, Sensor $S_9$ is a sensor which can detect the displacement, velocity, or acceleration of a muscle underlying the skin to which the sensor is secured. As disclosed herein, drugs are commonly administered to block shivering, so that the signal from Sensor $S_9$ normally equals substantially zero and thus need not be interpreted by the physician.

In one embodiment, Sensor $S_{10}$ (FIG. 2) is a thermometry sensor, which measures the local temperature of the patient's skin, where it is secured. Skin temperature is not generally a signal directly involved in the TTM control loop (feedback loop) described above, which maintains the patient core temperature substantially equal to the TTM Set Point Temperature. However, the skin temperature signal may give the physician useful information. Fundamentally, skin temperature serves as an important signal in the human thermoregulatory system; for example, it is believed to control shivering. Similarly, the time-rate-of-change of skin temperature is believed to be a distinct signal contributing to the control of shivering in humans (Fiala et al., 2001). The signal from Sensor $S_{10}$ optionally may processed by the Processor with a suitable low-pass filter to yield a signal that is substantially constant from second to second and thus contains no variations as rapid as many times per second. This processed signal is stored in the Memory, then it is display, as described above.

In another embodiment, thermometry sensors are placed at more than one location on the patient's skin. Then these values of temperature are processed by being averaged together, so as to give a more meaningful estimate of the average skin temperature of the entire patient. Optionally, the individual values of temperature measured at different locations of the body may be assigned different weighting factors with the intent of approximating the unequal weighting that the human thermoregulatory system gives to different skin temperatures (Tanabe et al., 2002).

In one embodiment, the temperature of the skin of a finger of the patient is measured by Sensor $S_{10}$. It has been reported that the finger temperature correlates closely with the degree of vasoconstriction in the underlying tissue in human subjects (Akata et al., 2004). Thus, the finger temperature is a proxy for a deeper physiological variable in human thermoregulation. The behavior of such a physiological variable is important to include the machine learning process described below, which seeks to deduce the changing Endogenous Set Point Temperature, and other fundamental values that define the physiological state of the patient.

In one embodiment, the values of skin temperature measured over time will be differentiated with respect to time, so as to give a distinct quantity believed significant in the human thermoregulatory system (Fiala et al., 2001). The differentiation can be performed approximately by applying known finite difference formulas, one such being $dT_{skin}/dt = (T_{skin}(n)-T_{skin}(n-1))/\Box t$, where $T_{skin}(n)$ is an arbitrary measured value of $T_{skin}$ in the steady stream of such values flowing from Sensor $S_{10}$ to the Processor, $T_{skin}(n-1)$ is the immediately preceding value in the stream, and $\Box t$ is the time interval between sampled values of $T_{skin}$, as determined by the ADC. More complicated formulas that express $dT_{skin}/dt$ with greater accuracy are known in the field of numerical methods (Hornbeck, 1975). The computed, estimated values of $dT_{skin}/dt$ are stored in Memory, then displayed, as described above.

The display of current and past values of both $T_{skin}$ and $dT_{skin}/dt$ may individually or together help the physician predict the onset of shivering in the patient, because both quantities are known to be significant in human thermoregulation. Shivering works again maintaining the hypothermic set point temperature, so the physician would like to anticipate shivering, then administer drugs to block it. The storage in memory and the display of current and past values of both $T_{skin}$ and $dT_{skin}/dt$ generally supports the effort to understand human thermoregulation, as well as the thermoregulation of a specific patient. As disclosed above, machine learning techniques generally are capable of extracting the complicated relationships between sets of input signals and output signals (Kato, 2009). In the clinical setting of Targeted Temperature Management, machine learning techniques could be applied to deduce the changing Endogenous Set Point Temperature (ESPT) of a patient from the stream of unprocessed and processed signal values using the sensors described above.

In one embodiment, Sensor $S_{12}$ measures the volume flow rate of expired gases from the patient and Sensor $S_{13}$ measures the concentration of oxygen in the expired gases from the patient. The ADC in the Processor samples these measurements at such a rate that will produce, for example, 100 samples per expiration of the patient. The Processor computes the product of the paired samples of (a) flow rate of the expired gases and (b) oxygen concentration of the expired gases. This product is numerically integrated over the duration of the expiration to yield a quantity equal to the number of moles of oxygen expired during each breath. Numerical integration can be performed according to known algorithms, one such being the trapezoid rule (Hornbeck, 1975). In a separate calculation, the volume flow rate is integrated numerically over one breath to give a quantity equal to the volume of the expired gases.

Next, the number of moles of oxygen inspired by the patient is computed as follows. The volume of inspiration is assumed to equal the computed volume of expiration defined above; the concentration of inspired oxygen is assumed to equal the standard value for the earth's atmosphere. Then the number of moles of inspired oxygen must equal the product of volume and concentration, as defined immediately preceding, and the Processor computes the number of moles inspired by the patient after each full breath.

The Processor computes the number of moles of oxygen consumed by the patient with each full breath by subtracting the moles of oxygen expired from the number of moles inspired. The Processor converts this number of moles consumed per full breath to a rate of consumption by dividing it by the time associated with each full breath; this time is defined by the difference of successive end-of-expiration times, the end of expiration time being defined by the time at which flow velocity drops to a value substantially equal to zero.

The Processor converts the value of moles of oxygen consumed per unit time to a value of liters of oxygen at standard temperature and pressure consumed per unit time by applying a known conversion factor. Specifically, it is known that consuming a liter of oxygen at standard temperature and pressure produces 4.825 kilocalories of energy in a human subject subsisting on an average diet (Hall, 1996), p 907; this energy is equivalent to 20.188 kilojoules. As an example, the typical resting oxygen consumption rate of a human equals 3.5 mL/(min kg), and this corresponds to 82 watts of energy consumption in a 70 kg person.

In an alternative embodiment, account will be taken of the particular proportions of carbohydrate, protein, and fat which are actually present in the diet of the patient, so as to compute a different value of kilocalories consumed per liter of oxygen than stated above for the average diet.

Through these equivalencies, the Processor will convert the measured rate of oxygen consumption to the rate of energy production by the patient. This rate of energy production substantially equals the metabolic energy production of the patient in the absence of any mechanical work performed. Optionally, the values of energy production will be processed by a suitable low-pass filter to yield values of energy production characteristic of a period of many minutes or several hours, as opposed for each breath. The values of rate of energy production will be stored in Memory and display, as described above.

In an alternative embodiment, the oxygen sensor $S_{13}$ measures the partial pressure of oxygen, not the concentration. In this embodiment, Sensor $S_{14}$ measures the temperature of the expired gases at the same instants at which the partial pressure of oxygen is measured. The Processor applies the Ideal Gas Law to compute values of the concentration of oxygen from values of the partial pressure of oxygen and its temperature, specifically, n/V=P/(R T), where n/V is the number of moles of oxygen per unit volume, P is the partial pressure of oxygen, R is the universal gas constant, and T is the temperature of the oxygen. With values of concentration known, the processing described in preceding paragraphs will be done to yield values of metabolic energy production.

In an alternative embodiment, the concentration of expired oxygen is treated for simplicity as a constant at all instants of expiration. The subsequent processing entails only multiplying this constant by the integrated value of volume flow rate, so as to yield a value for the number of moles of oxygen expired with each breath. The processing steps that follow next are as described above.

In one embodiment, the Processor computes the thermal energy of each expired breath, as follows. At each instant during expiration, the rate of thermal energy transport of the expired air is given by $\rho \, c_p \, w \, T_{air}$. The values of volume flow rate of expired gases measured by Sensor $S_{12}$ are paired by the Processor with values of the temperature of expired gases measured by Sensor $S_{14}$, so as to form the product of the two quantities at each instant of measurement. The resulting series of values is integrated numerically according to known methods described above, then multiplied by the specific heat of air and the density of air, both assumed to equal constants for simplicity. The result is the total thermal energy of the expired breath.

The rate of thermal transport associated with each inspired breath is computed by assuming that the volume of inspiration equals to volume of expiration, the later computed as described above. The temperature of the inspired air equals a constant value, namely the temperature of the ambient air, measured by sensor $S_8$. The total thermal energy of each inspired breath equals $\rho \, c_p \, V \, T_{air}$, where V is the volume of the breath, taken to equal the volume of the expired breath, as described. To quantify the thermal energy lost by the patient with each breath, the Processor subtracts the thermal energy of the most recent inspired breath from that of the most recent expired breath. The rate of energy loss is computed by dividing the energy loss just defined by the duration of the most recent full breath, meaning inspiration plus expiration. The duration of a full breath can be computed as defined above. The current and past values of the rate of energy loss by breathing are displayed as described above. Optionally, these values may be processed by a suitable low-pass filter in the Processor, so as to quantify the loss of thermal energy by breathing over the past several minutes or several hours, not the value of each breath.

In one embodiment, the density of air is treated as a varying function of air temperature, not as a constant. Consequently, for each instant when expired air flow rate and temperature are measured, the triple product $\rho(T) \, w \, T_{air}$ is computed, where the known functional dependence of the density of air on temperature is expressed as a look-up table or as a simple functional, such as a linear function or a quadratic function (Mills, 1999). As described previously, the constant $c_p$ multiplies the result, and all such products are integrated numerically, as described above, to compute the thermal energy of each expiration.

It will be appreciated that variations on the system described above are possible, including variations that are unnecessary and wasteful, for example, measuring the varying volume flow rate of the inspired air at many instants during inspiration. This is unnecessary and wasteful, because these measurements are performed on the expired air, and it must be so that the volume of the expired air must equal the volume of the inspired air in a patient with normal lungs.

In one embodiment, the partial pressure of water vapor in the expired air is measured by Sensor $S_{15}$ at many instants during each expiration, one example being 10 instants during expiration and another example being 100 instants during expiration. The Processor makes a calculation based on the Ideal gas Law to convert the partial pressure of water vapor to the concentration of water vapor using the value of expired air temperature measured at that instant by Sensor $S_{14}$, as explained above. Each such measurement of water vapor concentration is paired with the measurement of air flow rate made by Sensor $S_{12}$ at the same instant, then the two quantities are multiplied by the Processor, and finally the results are stored in Memory. All such results from the same expiration are integrated numerically, as described above, so as to express the total mass of water contained within the expired breath.

To compute the water content of the inspired breath, the volume of the inspired breath is taken to equal that of the expired breath, as described above. Then the value of partial pressure of water vapor of the ambient air measured by Sensor $S_{11}$ is converted to a value of concentration of water vapor by application of the Ideal Gas Law, using the value of ambient air temperature measured by Sensor Sa. The Processor multiplies the volume of the breath of inspired air by the concentration of water vapor to express the total water content of each inspired breath. The Processor subtracts the water content of the inspired breath from that of the expired breath to express the mass of water lost in that breath by the patient. This mass of water is converted to energy by multiplying by the known heat of vaporization of water, 2256 joules/gram (Halliday, 1966), p 563. The Processor converts this value of energy lost per breath to a rate of energy loss by dividing by the duration of the full breath, as described above. These values of energy loss due to evaporation in the lungs are displayed, as described above. Optionally, these values may be processed by a low-pass filter, as described above. In combination with the other energy expenditures described above, this display of thermal energy lost in respiration will help define the energy status of the patient, the better to allow detection of changes in this energy status. In addition, the application of machine learning techniques, as described above, may allow automated detection of changes in ESPT in the clinic.

In one embodiment, Sensor $S_{16}$ placed on the skin of the patient detects sweating, for example, by the value in electrical conductivity between closely-spaced electrodes. This signal is sampled by the ADC, stored in memory, optionally filtered by a low-pass filter designed to display the average value of the signal over the last several minutes or the last several hours, then displayed, as described above. It is not expected that a patient undergoing hypothermic TTM will sweat. However, the continuous display of a signal from Sensor $S_{16}$ that is consistent with no sweating will confirm the expected physiological state of the patient for the physician. By contrast, in the case of hyperthermia TTM, sweating may be an expected response by the patient.

Figure 4:
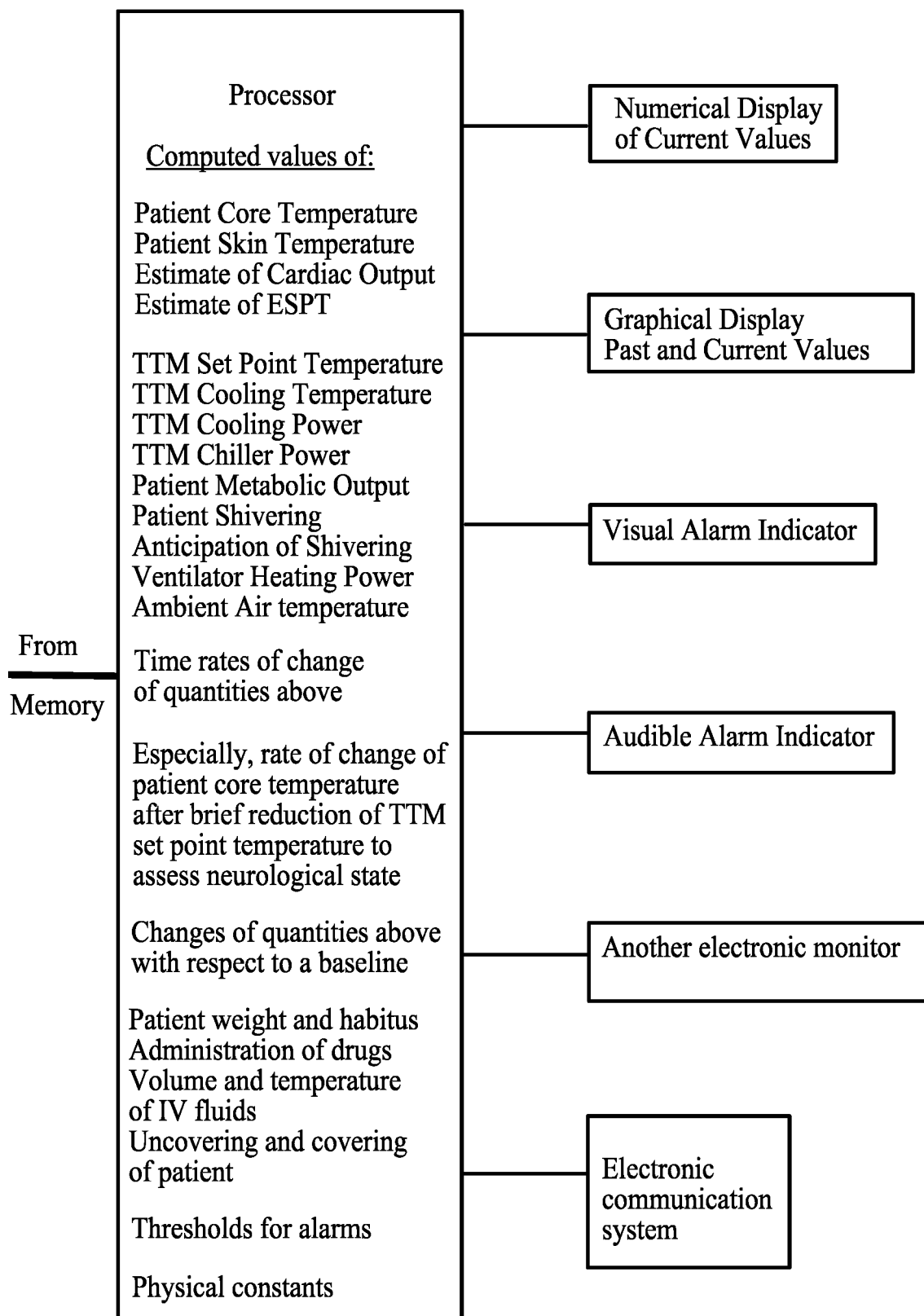
FIG. 4 is shows another example of a processor scheme useable in systems of the present invention.
Figure 5:
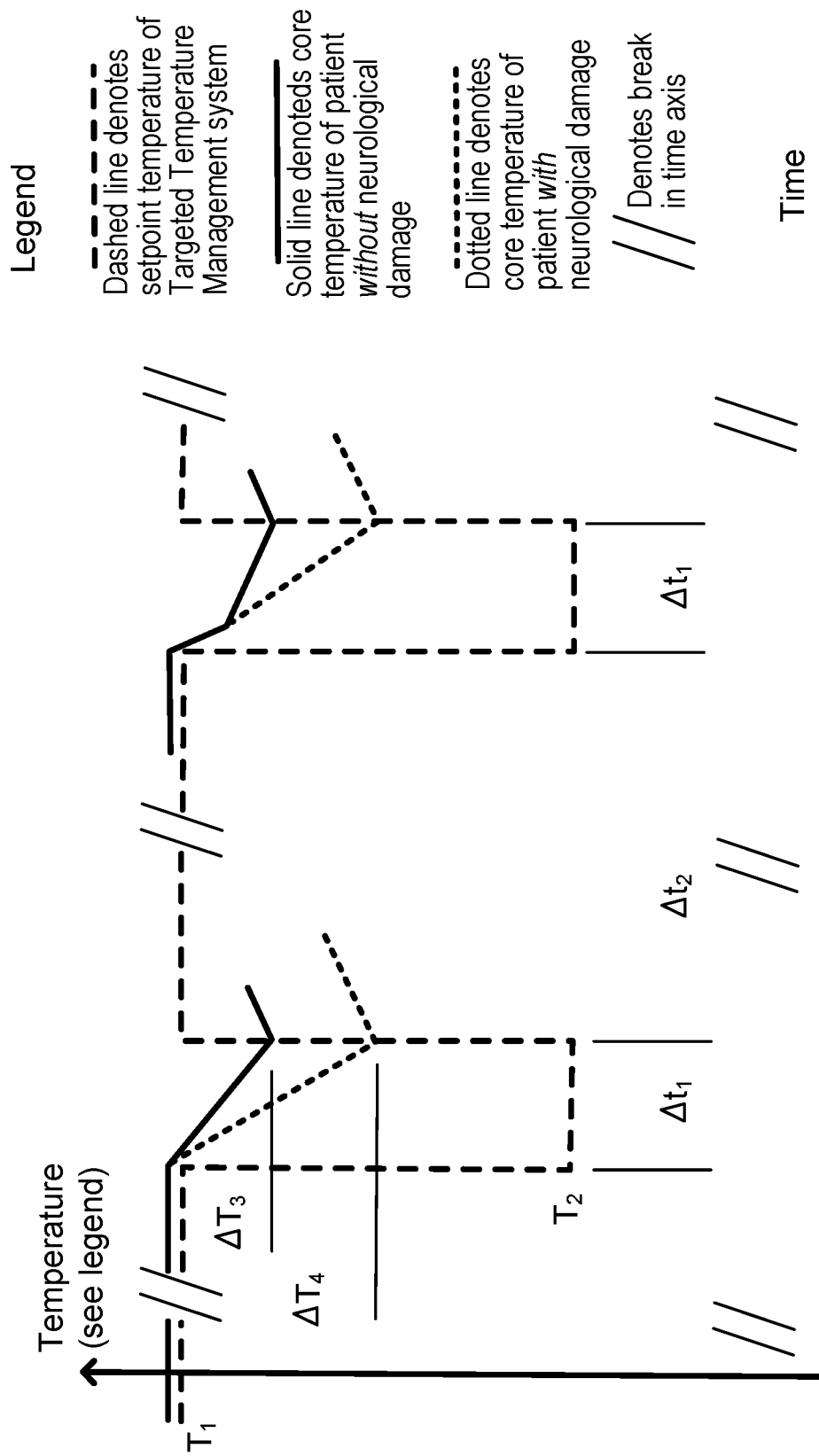
FIG. 5 shows a graphic example of responses of the core temperature of a normal patient and a patient with neurological deficits in response to a sudden decrease in TTM set point temperature.

In one embodiment, the neurological state of the patient is assessed indirectly, as follows. After the elapse of a certain time period, for example, every four hours, the set point temperature of the TTM system is reduced by a pre-determined value that does not change from instance to instance, for example, by 3° C. The duration of time during which the set point is reduced intentionally is too short to allow the patient's core temperature to attain the new set point temperature, for example, 5 minutes. The new set point temperature will be displayed as a rectangle waveform with the new, lower value described preceding. As discussed above, clinicians have observed that patients with neurological deficits will display a more rapid decrease of core temperature in response to this challenge than will patients will substantially full neurological functions. FIG. 5 shows the simplified responses of the core temperature of a normal patient and a patient with neurological deficits in response to a sudden decrease in TTM set point temperature; the TTM set point temperature has decreased suddenly from $T_1$ to $T_2$. As shown, the core temperature of the normal patient typically will decrease by a smaller amount, $\Delta T_3$, than the larger amount, $\Delta T_4$, of the patient with significant neurological deficit. In FIG. 5 4, $\Delta t_1$ is the duration of the time during which the lower set point temperature $T_2$ is applied; $\Delta t_2$ is the duration of time between transitions of the set point temperature.

At the end of the time period defined by $\Delta t_1$, the Processor will compute the slope defined by $\Delta T_3/\Delta t_1$, then store and display its value for comparison to all previous times at which the TTM set point was lowered suddenly from $T_1$ to $T_2$. The equation defining the slope could equally well be written as $\Delta T_4/\Delta t_1$, using the terminology of FIG. 4, because the neurological status of the patient is not known a priori. The sequence of slope values that result from this procedure may be usefully plotted against time, so as to make a trend apparent to the physician. A trend of more negative values of slope would suggest increasing neurological deficit, and a trend of less negative values of slope would suggest the opposite.

It will be appreciated that certain embodiments disclosed herein could be embodied in a different type of TTM system which cools the patient with external pads applied to the torso and limbs of the patient, rather than with an intravenous catheter placed within the patient. Most importantly, the expression defining the cooling power applied to the patient by the TTM system does not change. As described above, $$P_{cool} = c_p \rho w (T_{outflow} - T_{inflow})$$

wherein $T_{inflow}$ is the coolant temperature flowing into the cooling pads, and $T_{outlet}$ is the coolant temperature flowing out of the cooling pads. Given this physical equivalence, the disclosures above pertaining to the TTM system using the intravenous catheter will apply also to a TTM system using external cooling pads.

In one embodiment, manual entry of relevant information into Memory for the purpose of calculation or display will be made possible by a keypad or equivalent device. Manual entry will be performed to store relevant information that is not convenient to measure with the sensor described above. In particular, it is useful to enter the value of the TTM set point temperature at such times when it is changed by the physician managing the care of the patient. This value of temperature will be stored in memory, then displayed with the current and recent values of the core temperature of the patient. With this display, the physician can confirm the successful maintenance of the TTM treatment at all times. As disclosed above, the neurological condition of the patient may be assessed in the times immediately following periodic and temporary changes in the TTM set point temperature.

Other relevant information that may be entered manually into Memory for processing and display is: (a) patient weight and habitus, parameters that generally affect heat transfer from the patient, (b) type, amount, and time of administration of drugs that block the shivering response of the patient, (c) type, amount, and time of administration of all other drugs, (d) temperature, volume, and time of administration of all intravenous fluids, these representing heat transfer to or from the patient, and (e) covering, uncovering, and repositioning of the patient, these being factors that affect heat transfer from the patient through changes in the thermal insulation of the patient.

In an alternative embodiment, the values of the set point temperature are accessed electronically within the TTM system, not by manual entry. Then its values are stored in Memory and displayed, as described above.

Although the invention has been described hereabove with reference to certain examples or embodiments of the invention, various additions, deletions, alterations and modifications may be made to those described examples and embodiments without departing from the intended spirit and scope of the invention. For example, any elements, steps, members, components, compositions, reactants, parts or portions of one embodiment or example may be incorporated into or used with another embodiment or example, unless otherwise specified or unless doing so would render that embodiment or example unsuitable for its intended use. Also, where the steps of a method or process have been described or listed in a particular order, the order of such steps may be changed unless otherwise specified or unless doing so would render the method or process unsuitable for its intended purpose. Additionally, the elements, steps, members, components, compositions, reactants, parts or portions of any invention or example described herein may optionally exist or be utilized in the absence or substantial absence of any other element, step, member, component, composition, reactant, part or portion unless otherwise noted. All reasonable additions, deletions, modifications and alterations are to be considered equivalents of the described examples and embodiments and are to be included within the scope of the following claims.

What is claimed is:

1. A system for controlling a patient's temperature and determining a neurological deficit in the patient, the system comprising:
 a body heat exchanger configured to exchange heat with the patient's body by circulating heat exchange fluid through the body heat exchanger;
 a sensor for measuring a core temperature of the patient; and
 a control apparatus for controlling the body heat exchanger to maintain the core temperature of the patient at a target temperature or within a target temperature range, the control apparatus including a processor configured to:
  temporarily change the target temperature; and
  determine a rate of change of the patient's core temperature response to a temporary change in the target temperature to determine the neurological deficit in the patient.

2. The system according to claim 1, wherein the control apparatus is further configured to periodically apply the temporary change in the target temperature and determine the rate of change of the patient's core temperature response therefrom.

3. The system according to claim 2, wherein the control apparatus is further configured to determine a trend in the rate of change of the patient's core temperature.

4. The system according to claim 2, wherein the control apparatus is configured to determine the neurological deficit in the patient by comparing the rate of change of the patient's core temperature response to the temporary change in the target temperature to a rate of change of a core temperature response of a patient without a neurological damage.

5. The system according to claim 1, wherein the control apparatus is further configured to temporarily reduce the target temperature for a duration too short to allow the patient's core temperature to attain the target temperature.

6. The system according to claim 5, wherein temporarily reducing the target temperature includes a reduction in the target temperature by about 3° C.

7. The system according to claim 1, wherein the body heat exchanger comprises a body surface heat exchange system.

8. The system according to claim 1, wherein the control apparatus is configured to temporarily change the target temperature for about 5 minutes.

9. A method for controlling a patient's temperature and determining a neurological deficit in the patient, the method comprising:
   circulating a heat exchange fluid through a body heat exchanger configured to exchange heat with a patient's body;
   measuring a core temperature of the patient;
   controlling the body heat exchanger to maintain the core temperature of the patient at a target temperature;
   temporarily changing the target temperature; and
   determining a rate of change of the patient's core temperature response to the temporary change in the target temperature to determine a neurological deficit in the patient.

10. The method according to claim 9, further comprising periodically applying the temporary change in the target temperature and determining the rate of change of the patient's core temperature response therefrom.

11. The method according to claim 10, further comprising determining a trend in the rate of change of the patient's core temperature.

12. The method according to claim 11, wherein a negative trend indicates increasing neurological deficit in the patient.

13. The method according to claim 11, further comprising periodically applying the temporary change in the target temperature and determining the rate of change of the patient's core temperature response therefrom.

14. The method according to claim 9, determining the neurological deficit in the patient includes comparing the rate of change of the patient's core temperature response to the temporary change in the target temperature to a rate of change of a core temperature response to the temporary change in the target temperature of a patient without the neurological deficit.

15. The method according to claim 14, wherein temporarily reducing the target temperature includes lowering the target temperature by about 3° C.

16. The method according to claim 9, wherein temporarily changing the target temperature includes temporarily reducing the target temperature for a duration too short to allow the patient's core temperature to attain the target temperature.

17. The method according to claim 9, wherein temporarily reducing the target temperature includes reducing the target temperature for about 5 minutes.

18. The method according to claim 9, wherein circulating the heat exchange fluid through the body heat exchanger includes circulating the heat exchange fluid through a body surface heat exchange system.

* * * * *